US012622935B2

(12) United States Patent
Ranki et al.

(10) Patent No.: US 12,622,935 B2
(45) Date of Patent: *May 12, 2026

(54) MODIFIED ONCOLYTIC ADENOVIRUSES

(71) Applicant: Valo Therapeutics Oy, Helsinki (FI)

(72) Inventors: Tuuli Ranki, Helsinki (FI); Sari Pesonen, Helsinki (FI); Petri Priha, Helsinki (FI); Erkko Ylösmäki, Helsinki (FI); Vincenzo Cerullo, Helsinki (FI); Beatriz Martins, Helsinki (FI)

(73) Assignee: VALO THERAPEUTICS OY, Helsinki (FI)

( * ) Notice: Subject to any disclaimer, the term of this patent is extended or adjusted under 35 U.S.C. 154(b) by 1141 days.

This patent is subject to a terminal disclaimer.

(21) Appl. No.: 17/040,017

(22) PCT Filed: Mar. 19, 2019

(86) PCT No.: PCT/EP2019/056768
§ 371 (c)(1),
(2) Date: Sep. 21, 2020

(87) PCT Pub. No.: WO2019/179977
PCT Pub. Date: Sep. 26, 2019

(65) Prior Publication Data
US 2021/0017501 A1 Jan. 21, 2021

(30) Foreign Application Priority Data

Mar. 21, 2018 (GB) ..................................... 1804473
Sep. 13, 2018 (GB) ..................................... 1814867

(51) Int. Cl.
*A61K 35/761* (2015.01)
*A61P 35/00* (2006.01)
*C07K 14/705* (2006.01)
*C12N 15/86* (2006.01)

(52) U.S. Cl.
CPC ...... *A61K 35/761* (2013.01); *C07K 14/70575* (2013.01); *C07K 14/70578* (2013.01); *C12N 15/86* (2013.01); *A61P 35/00* (2018.01); *C12N 2710/10321* (2013.01); *C12N 2710/10332* (2013.01); *C12N 2710/10371* (2013.01)

(58) Field of Classification Search
CPC ............ A61K 35/761; C07K 14/70575; C07K 14/70578; C12N 15/86; C12N 2710/10321; C12N 2710/10332; C12N 2710/10371; A61P 35/00
USPC ................ 424/199.1, 233.1, 93.2; 435/320.1
See application file for complete search history.

(56) References Cited

U.S. PATENT DOCUMENTS 12,031,145 B2 * 7/2024 Ranki .................... C12N 15/86
2004/0213764 A1 10/2004 Wold et al.
2018/0185515 A1 * 7/2018 Hicklin ............ C07K 14/70575

FOREIGN PATENT DOCUMENTS

WO WO 2014/170389 10/2014
WO 2016/146894 * 9/2016
WO WO 2017/205875 11/2017
WO WO 2018/046803 3/2018

OTHER PUBLICATIONS

Robinson et al. (2008) Canc. Gene Ther., vol. 15: 9-17.*
Jiang et al. (2005) Neoplasia, vol. 7(8):723-729.*
Zhou et al. (2017) Frontiers Immunol., vol. 8, article 983, doi: 10.3389/fimmu. 2017.00983, pp. 1-14.*
Alemany, "Molecular Design of Oncolytic Adenoviruses," Adenoviral Vectors for Gene Therapy, Academic Press, pp. 319-334, 2016.
De Graaf et al., "Armed oncolytic viruses: A kick-start for anti-tumor immunity," *Cytokine Growth Factor Rev* vol. 41:28-39, 2018.
Diaconu et al., "Immune Response is an Important Aspect of the Antitumor Effect Produced by a CD40L-Encoding Oncolytic Adenovirus," *Cancer Res.*, vol. 72:2327-2338, 2012.
Elsevier website, press release, "Elsevier hits the mark with ScienceDirect Topics," available online at http://scitechconnect. elsevier.com/elsevier-hits-the-mark-with-sciencedirect-topics/ (accessed Sep. 24, 2018), 3 pages.
Robinson et al., "Comparison of the E3 and L3 Regions for Arming Oncolytic Adenoviruses to Achieve a High Level of Tumor-Specific Transgene Expression," *Cancer Gene Ther.*, vol. 15:9-17, 2008.
Science Direct Website, Oncolytic Adenovirus page, "Learn more about Oncolytic adenovirus," available online at https://www. sciencedirect.com/topics/immunology-and-microbiology/oncolytic-adenovirus (accessed Sep. 24, 2018), 9 pages.
International Search Report and Written Opinion from PCT/EP2019/056768, mailed Sep. 26, 2019, 17 pages.
International Preliminary Report on Patentability from PCT/EP2019/056768, mailed Mar. 12, 2020, 15 pages.
United Kingdom Intellectual Property Office search report from GB Application No. 1804473.5, dated Sep. 27, 2018, 5 pages.
Bett et al., "Packaging Capacity and Stability of Human Adenovirus Type 5 Vectors," *J Virol* 67(10):5911-5921, 1993.
Haut et al., "A Partial E4 Deletion in Replication-Defective Adenoviral Vectors Allows for Stable Expression of Potentially Toxic Transgene Products," *Hum Gene Ther Methods* 27(5):187-196, 2016.
Zhu et al., "Linked Tumor-Selective Virus Replication and Transgene Expression from E3-Containing Oncolytic Adenoviruses," *J Virol* 79(9):5455-5465, 2005.

* cited by examiner

*Primary Examiner* — Anne Marie S Wehbe
(74) *Attorney, Agent, or Firm* — Klarquist Sparkman, LLP

(57) ABSTRACT

The invention concerns a modified replication competent, oncolytic adenovirus; a pharmaceutical composition comprising same; and a method of treating cancer using same.

11 Claims, 8 Drawing Sheets

Figure 1:
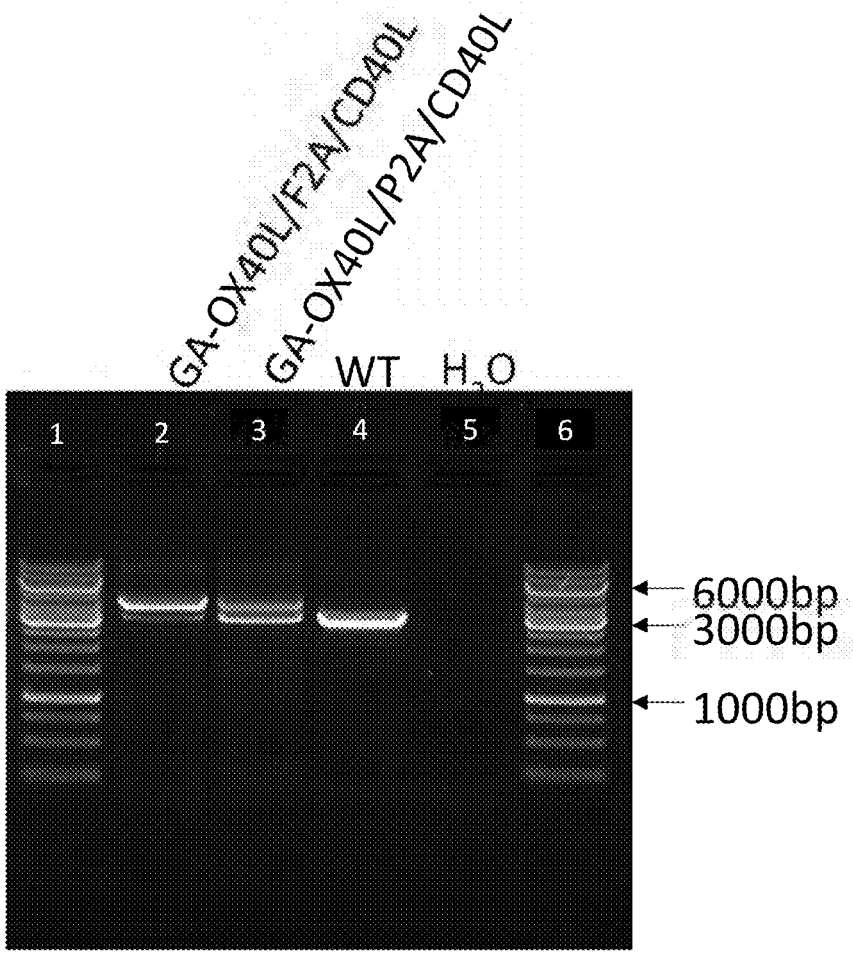

Specification includes a Sequence Listing.

FIG. 2A                    FIG. 2B

FIG. 3
Functional ELISA for OX40L
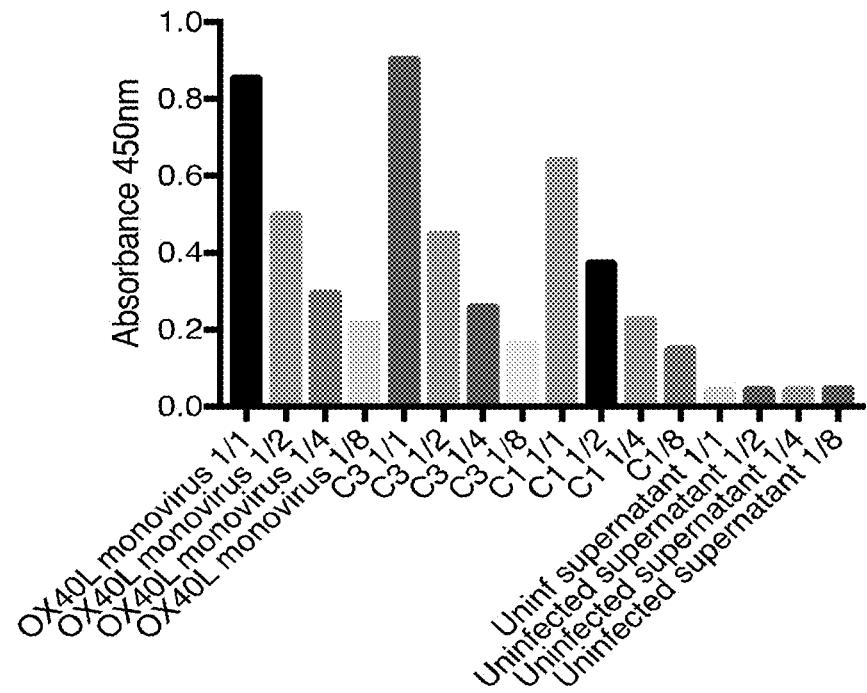
OX40L Func. Assay
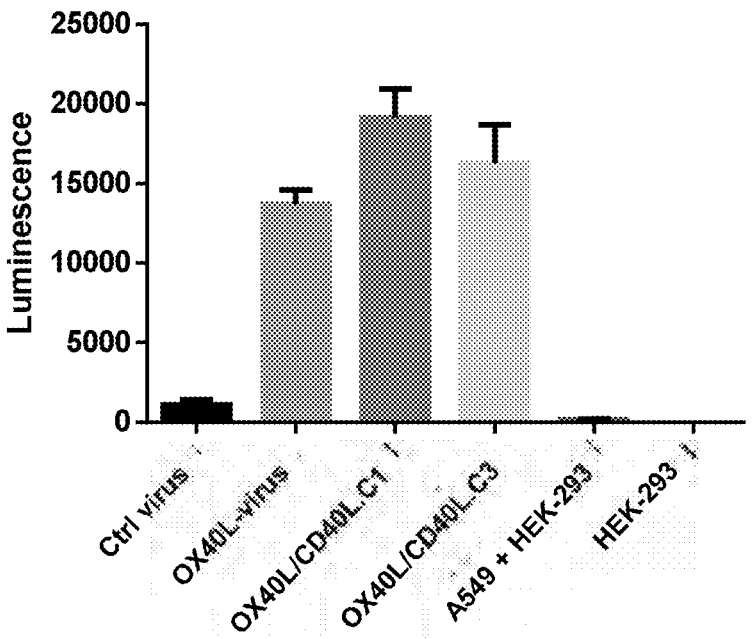
FIG. 4

FIG. 7A
FIG. 7B
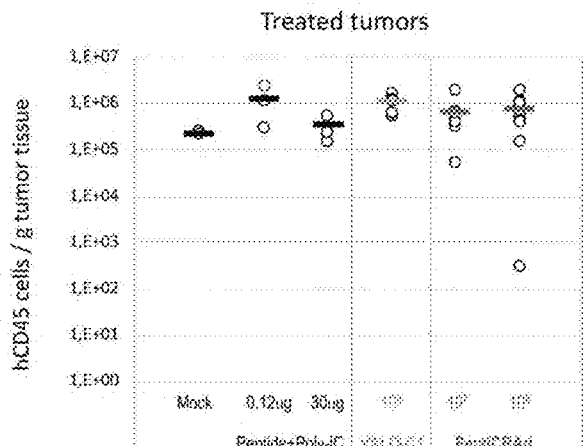
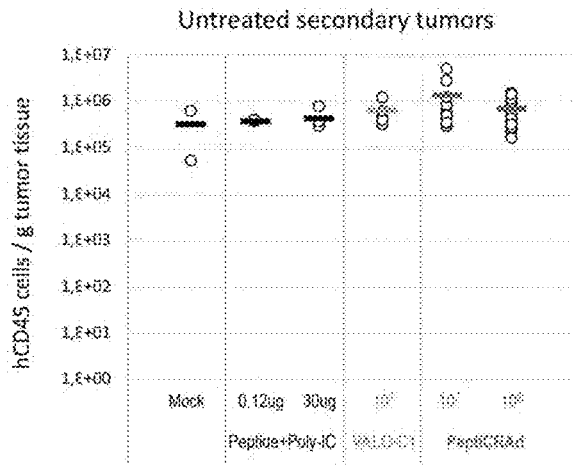
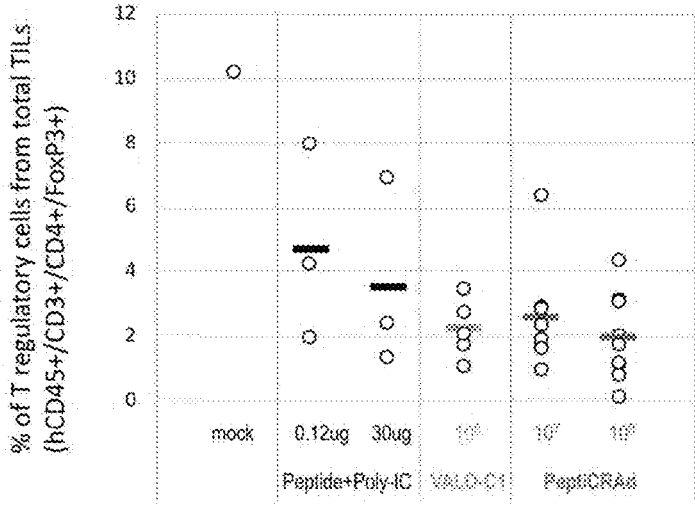
FIG. 8

FIG. 9
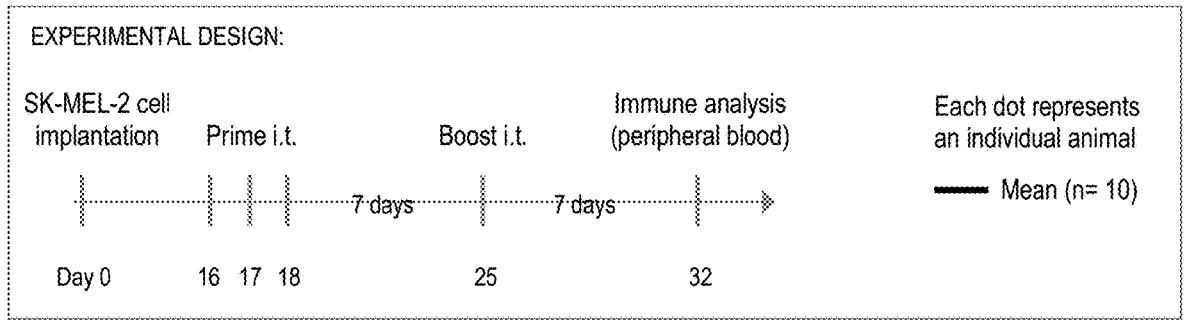
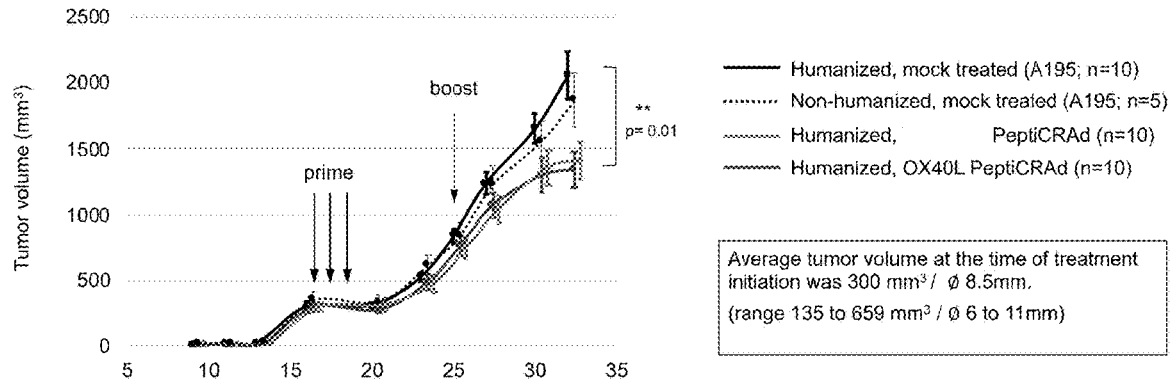

MODIFIED ONCOLYTIC ADENOVIRUSES

CROSS REFERENCE TO RELATED APPLICATIONS

This is the U.S. National Stage of International Application No. PCT/EP2019/056768, filed Mar. 19, 2019, which was published in English under PCT Article 21 (2), which in turn claims the benefit of Great Britain Application No. 1814867.6, filed Sep. 13, 2018, and Great Britain Application No. 1804473.5, filed Mar. 21, 2018.

Incorporation of Electronic Sequence Listing

The Sequence Listing is submitted as an ASCII text file, created on Sep. 17, 2020, 4.94 KB, which is incorporated by reference herein.

FIELD OF THE INVENTION

The invention concerns a modified replication competent, oncolytic adenovirus; a pharmaceutical composition comprising same; and a method of treating cancer using same.

BACKGROUND OF THE INVENTION

The perception of the role of oncolytic viruses in cancer treatment has changed dramatically during the last decade, as immunotherapy and the stimulation of the patient's own immune system to target and attack cancer has gained popularity. At the beginning of the century, oncolytic viruses were perceived as active agents in cancer treatment, acting solely through their inherent ability to lyse tumor cells via oncolysis. Recently, their use as cancer vaccines has gained interest, and their ability to release tumor antigens from cancer cells upon oncolysis for activating the immune system is recognised as an important characteristic in designing the ultimate immunotherapy against cancer.

Adenoviruses are highly immunogenic viruses often used as vectors in various vaccine approaches against infectious diseases. Importantly, they have an exceptional ability to both prime and boost immune responses. Further, the presence of an oncolytic adenovirus within a tumor and the immunogenic cell death it causes is likely to shape the hostile tumor microenvironment towards a more susceptible state for a clinically relevant anti-tumor immunity to occur, by causing the expression of TH1-type immune modulators such as interferon gamma (IFNgamma). Immune cell infiltration to tumor is a frequent consequence of treatment with oncolytic viruses, and importantly, adenoviruses induce the infiltration by CD8+ T cells that are key effector cells in cancer immunity. Adenoviruses cause immunogenic cancer cell lysis whereupon tumor antigens, including unique patient specific neoantigens, previously hidden from the immune system or not presented in an immunogenic context are released into the immunogenic environment. This is the basis for a tumor-specific immune response caused by oncolytic adenoviruses.

However, tumors have evolved several immunosuppressive mechanisms to counteract the immune cells of the body. Immune cells express cell surface molecules that regulate their activation and effector functions, specifically co-stimulatory and co-inhibitory molecules. The negative feedback molecules, i.e. checkpoint molecules, enable self-tolerance under normal physiological contexts, but are often utilized by the tumor cells to cause severe immune suppression. The best characterized checkpoint pathways are cytotoxic T-lymphocyte protein 4 (CTLA-4) and programmed cell death protein 1 pathway (PD-1/PD-L1). Due to these strong immunosuppressive mechanisms within the tumor, the virus-induced anti-tumor immune response can be weak unless strengthened by the use of immunostimulatory transgenes. The current approach tackles the problem of immune suppression at the tumor site, as the presence of the highly immunogenic oncolytic adenovirus encoding immunostimulatory human transgenes shapes the tumor microenvironment towards an "immune inflamed" phenotype that is more susceptible towards immunotherapy approaches. Importantly, the oncolytic virus of the current approach can be utilized in combination with checkpoint modulators such as anti-PD1, anti-PD-L1 or anti-CTLA-4 molecules to counteract immunosuppressive tumor environment and to cause a strong anti-immune response.

STATEMENTS OF THE INVENTION

According to a first aspect of the invention there is provided a modified, replicating adenovirus having lytic activity in target cancer cells comprising:
  a) a E1A gene deletion wherein the deletion is of nucleotides encoding amino acids 923-946;
  b) a 5/3 chimeric substitution of a knob of an adenoviral fiber protein wherein the knob of serotype 5 Ad is replaced by the knob of a serotype 3 Ad;
  c) a 14.7k gene deletion wherein the deletion is of base pairs 30448-30834 with respect to the wild type adenovirus and wherein the sequence GGA GGA GAT GAC TGA (SEQ ID NO: 1) is substituted for GGA GGA GAC GAC TGA (SEQ ID NO: 2); and
  d) a gp19k gene deletion and a 7.1k gene deletion wherein the deletions are of base pairs 28541-29211 with respect to the wild type adenovirus.

In the above modified adenovirus amino acids 923-946 are deleted from the wild type (wt) Ad5 sequence. This deletion is a safety measure: as the viral E1A protein cannot bind to a retinoblastoma (Rb) molecule and release the transcription factor E2F from Rb for viral gene transcription. Thus the adenovirus relies on the presence of free E2F in a host cell, and can replicate its genome in either dividing normal cells or in cancer cells, where free E2F is constantly available. Thus the modification is relatively protective of non-dividing cells and targeted against dividing or cancer cells.

Additionally, the 5/3 chimeric substitution i.e. replacing the serotype 5 adenoviral fiber knob region with that of a serotype 3 adenovirus knob region; allows the virus to circumvent the Ad5 native receptor coxsackie-adenovirus receptor (CAR) and to use the Ad3 native receptor desmoglein 2 (DSG2) for internalisation instead. DSG2 is present abundantly in cancer cells. Thus again the modification is relatively protective of non-dividing cells and targeted against dividing or cancer cells.

Adenoviral infection commences with recognition of host cell receptors by means of specialised proteins on the viral surface i.e. the adenovirus fibre protein and in particular the globular carboxy-terminal domain of the adenovirus fibre protein, termed the carboxy-terminal knob domain. Accordingly, reference herein to a knob of an adenoviral fiber protein is reference to the globular carboxy-terminal domain of the adenovirus fibre protein.

Moreover, the 14.7k gene deletion prevents infected cells from dying by TNFalpha induced cytolysis, and thus the deletion is advantageous. Importantly, we have observed there is a short overlap in the beginning of the 14.7k gene and the upstream RID beta (14.5k) gene and thus a modification is undertaken to allow deletion of the 14.7k gene without deleting the last amino acid and the stop codon of RID beta gene. Specifically, the native junction sequence reads as (SEQ ID NO: 3)

GGAGGAGATGACTGATTAGGTA with, the underlined sequence being the C-terminus of the RID beta gene and the remainder being the N-terminus of 14.7k gene. The translation to amino acids reads as G G D D stop (GGA GGA GAT GAC TGA; SEQ ID NO: 1) for the RID beta gene. Thus to abrogate the ATG within the ORF of the RID beta gene so that there is no incorrect read through if a transgene is inserted within the deletion site, and to make sure that we keep the C-terminus of the RID beta functional we have changed the sequence of the RID beta slightly: GGA GGA GAC GAC TGA (SEQ ID NO: 2). This way the sequence still reads as G G D D stop but does not contain an ATG for any incorrect downstream read-through that might interfere with transgene expression.

Finally, gp19k is a gene that downregulates MHCI on the infected cell, and it is redundant for adenovirus replication, packaging etc and thus can be removed. Further, as it is an immunoregulatory gene which adenovirus uses to hide from the immune system, it is beneficial to delete it. 7.1k is a gene related to the degradation of TRAIL receptor 2 and inhibits apoptosis induced by Ca2+ release from the endoplasmic reticulum (ER). However, as the stop codon of the 7.1k gene resides within the open reading frame of gp19k, no transgenes are added to this deleted site.

In a preferred embodiment of the invention said adenovirus is further modified by the insertion of a molecule encoding OX40L, ideally human OX40L, in the 14.7k gene deletion. OX40L is a T cell activator and so is advantageous to the functioning of the invention.

The OX40L gene has its own start codon (ATG) and when inserted into the 14.7k gene deletion it is preferred that a CC base pairing is added in between the stop codon of RID beta gene and the start codon of OX40L to optimize translation (i.e. to generate Kozak sequence ACCATGG).

Most preferably, the human OX40L is situated in the E3B region, replacing the gene 14.7K deletion. The 3'-end of the RID beta gene and the 5'-end of the 14.7K are overlapping in the wt adenovirus, and thus the T/C modification explained above was made to the 3'end of RID beta, to allow correct transcription of the transgene.

In yet a preferred embodiment of the invention said adenovirus is alternatively or additionally modified by the insertion of CD40L, ideally human CD40L. The human CD40L is inserted in the late region of the virus, specifically in the late region 3 (L3), ideally, downstream from the 23K gene, or in the L5 region, downstream from the Fiber gene. CD40L activates Antigen Presenting Cells (APCs) and so is advantageous to the functioning of the invention.

Preferably, transgene CD40L is situated immediately after the coding region of the adenoviral 23K gene, preceding its polyadenylation site, or immediately after the Fiber gene, preceding its polyadenylation site. Typically, but not exclusively, no deletions are made to accommodate the gene, and thus the expression of the transgene is dependent on the adenoviral alternative splicing machinery and a splice acceptor site (SAS) preceding the transgene (e.g. SAS adapted from US2006/0292682 A1 and WO2006/012393).

In yet a preferred embodiment of the invention said adenovirus is further modified by the insertion of a splice acceptor site (SAS) and/or a Kozak sequence upstream of the transgene CD40L to aid transcription of CD40L.

Alternatively and most preferably still, the CD40L transgene is inserted immediately downstream from OX40L using either
  A) a foot-and-mouth disease virus 2A processing site (F2A) (e.g. please see Ad5/3-D24-OX40L-F2A-CD40L, construct C1 in the figures) or
  B) Porcine teschovirus-1 2A processing site (P2A) (e.g. please see Ad5/3-D24-OX40L-P2A-CD40L, construct C3 in the figures).

The 2A processing site is inserted between the two transgenes and, ideally, both the 2A processing sites are preceded by a cleavage site (e.g. a furin cleavage site: RKRR, SEQ ID NO: 29) and a SGSG-linker (SEQ ID NO: 28) to ensure effective cleavage of the transgenes.

Those skilled in the art will appreciate that 2A processing sites are "self-cleaving" small peptides found in picornaviruses. Host ribosomes skips the synthesis of the glycyl-prolyl peptide bond at the C-terminus of the 2A peptide, leading to the cleavage between a 2A peptide and its immediate downstream peptide. As a result, the cleaved-off downstream peptide has proline at its N-terminus, meaning that the CD40L protein produced from the virus constructs described herein has a proline at its N-terminus.

Accordingly, in a preferred embodiment of the invention said modified adenovirus includes one and more preferably two transgenes: OX40L and CD40L. Further, typically but not exclusively, said CD40L transgene is provided almost immediately or immediately downstream of said OX40L transgene or vice versa.

T cell receptor engagement by antigen-MHCI/II complexes constitutes the main signal, signal 1, for the activation of naive T cells. However, signal 1 is not sufficient to initiate productive generation and maintenance of effector T cells. Full activation of CD8+ T cells requires additional signals driven by co-stimulatory molecules present on activated APCs or helper T cells but rarely on tumors. The co-stimulatory molecules we have chosen to use as transgenes in our invention, i.e. CD40L and OX40L, are members of the tumor necrosis factor (TNF) superfamily of ligands. The majority of TNF superfamily ligands are predominantly expressed on cells involved in the immune system including B cells, T cells, natural killer (NK) cells, monocytes and DCs.

OX40 ligand (OX40L) and CD40 ligand (CD40L) are type II transmembrane proteins that have a relatively long extracellular domain and a short cytoplasmic region. The extracellular domain (specifically, the TNF homology domain) displays the receptor binding specificity that is essential to the functionality of the ligand. Most TNF superfamily ligands are expressed as homotrimers on the cell surface, and are inactive or poorly active as soluble trimeric fusion proteins. Thus, a soluble form without the transmembrane region would not be applicable for our approach. Therefore, in the present invention, the whole cDNA of each transgene is utilized. This way, the transgene products contain all the domains that are naturally present in the protein that is produced from a cell, i.e. also a transmembrane domain that directs the protein to the secretory pathway and retains it in the cell membrane, as well as the naturally occurring sites that cause cleavage from the cell surface by proteinases.

Accordingly, in a preferred embodiment of the invention a molecule encoding the whole of at least one or each transgene is inserted into said adenovirus, ideally cDNA encoding the whole of at least one or each transgene.

Mostly the approaches that utilize co-stimulator molecules as the therapeutic agent to elicit/enhance anti-tumor immunity, use either monoclonal agonist antibodies specific for receptors of the TNF ligands, or soluble forms of the ligands. This approach requires the systemic delivery of the therapeutic molecules. In contrast, our approach resembles the natural situation within the body, where the ligands are presented to their cognate receptors as membrane tethered proteins produced by the cellular machinery of the infected cancer cell.

CD4+ T cells play a crucial role in the maintenance of an effective CD8+ T cell response in persistent viral infections. The novel viral construct of the invention with costimulator transgene(s) elicits Th1-type anti-viral immunity within the tumor environment. The presence of tumor antigens on the surface of the virus and the release of other tumor antigens in the presence of local inflammation, as well as determinant spreading, leads to the formation of anti-tumor immune T cell clones. In order to maintain the effector phase of the CD8+ cytotoxic T cells, costimulatory molecules (namely OX40L and CD40L) possess unique features that we want to apply in the treatment of immunosuppressive cancer.

Surprisingly, our data indicates that the addition of the immunostimulatory transgenes, human OX40L and human CD40L, into the 14.7K locus does not compromise the oncolytic efficacy of the viruses of the present invention, when compared to the backbone virus Ad5/3D24 or a virus with an immunostimulatory transgene, e.g. human GM-CSF, replacing the deleted gp19K/7.1K genes. This is surprising because the transgenes may affect the virus replication profoundly due to the size of the transgene and the direct effects of the transgene on the cells that are infected. Additionally, the deletion of the 14.7K gene is not as extensively studied as the deletion of gp19K/7.1K genes and thus might have unexpected consequences for the replicative machinery of the virus, especially in the context of incorporating transgenes in the 14.7K deletion site.

We also show that the virus of the present application is able to produce functional human transgenes from the 14.7K gene locus. This was unexpected because we used, somewhat unusually, a transcription cassette with a viral 2A processing site in between the two transgenes.

Further, we show that the virus of the present invention is able to elicit a MAGE-A3 and NY-ESO-1-specific immune response.

Accordingly, in a further aspect the invention concerns a pharmaceutical composition comprising at least one a replication-competent and target cell lytic adenovirus according to the invention and a suitable carrier.

OX40/OX40L

OX40L is expressed on activated APCs, including dendritic cells, B cells and macrophages. It is expressed on the cell surface as a trimer allowing it to bind to three OX40 molecules. T cell activation is required for the expression of OX40, the receptor for OX40L, on CD8+ and CD4+ T cells. The induction of OX40 occurs within 24 hours and peaks 48-72 hours following initial TCR stimulation, and typically lasts 3-4 days. The relative level of OX40 receptor expressed on T cells is greatly influenced by the local environment via contact with professional antigen presenting cells expressing CD80 or CD86, or via a milieu rich in TNFalpha or similar inflammatory cytokines. Further, OX40L expression is normally primarily found at the site of inflammation. Thus, OX40 expressing T cells that are activated via TCR signalling receive co-stimulation via OX40L at the site of inflammation. This specificity of co-stimulation via OX40 is analogous to a danger signal received from an inflammatory environment, and thereby adds a layer of safety to its use. Further, the temporal expression of OX40 on T cell surface after the priming event suggests its importance in late proliferation and survival of effector T cells. The activation of the anti-apoptotic molecules BCL-2, BCL-xL, and survivin in OX40-stimulated T cells is suggested to be responsible for the increased clonal expansion and a larger pool of memory T cells.

CD40/CD40L

In addition to providing co-stimulatory signals directly to T cells, it also is attractive to promote activation of APCs that are likely cross-presenting tumor antigen so that increased co-stimulatory ligand expression is achieved in situ. CD40 is crucial for the function of B cells and of DCs that express it constitutively. CD40 ligand (CD40L) is principally expressed on activated T helper cells. Ligation of CD40 has been shown to license APCs and enable them to drive effector CTL responses, in part through the induction of IL-12 secretion but also through up-regulation of B7 family members (CD80, CD86). CD40/CD40L co-stimulation is important for induction of effective anti-tumor T-cell responses, and the incorporation of CD40L into tumor cell-based vaccines has been shown to significantly enhance immune responses to poorly immunogenic tumors in mice, underlining the importance of the indirect effect on adaptive immunity via APC in anti-tumor immunity.

In yet a further preferred embodiment of the invention said adenovirus may be of any type and species of adenoviridae e.g. not limited to human adenovirus but most typically is human adenovirus. Most favourably, the adenoviruses are capable of replicating and killing cancer cells while diverting the anti-viral immune response against the tumour.

It follows from the above that the modified adenovirus of the invention has been engineered to stimulate an immune response against cancer and specifically in a tumour environment where, typically, the immune system is compromised by the evasive mechanisms employed by the cancer cells.

In a preferred embodiment of the invention said virus has at least one of the following polypeptides attached covalently or non-covalently onto the viral capsid without having been genetically encoded by said adenoviral vector i) VFGIELMEVDPIGHLYIFAT [SEQ ID NO:1];
    ii) YLAMPFATPMEAELARRSLA [SEQ ID NO:2];
    iii) RGPESRLLEFYLAMPFATPM [SEQ ID NO:3] or
    iv) a polypeptide that is at least 60% identical therewith.

Accordingly, in yet a further aspect the invention concerns a method of treating cancer in a patient comprising administering to a patient an effective amount of a composition comprising at least one replication-competent and target cell lytic modified adenovirus according to the invention.

Additionally, or alternatively still, the invention concerns at least one replication-competent and target cell lytic modified adenovirus according to the invention for use in treating cancer.

Additionally, or alternatively, the invention concerns the use of at least one replication-competent and target cell lytic modified adenovirus according to the invention to treat cancer.

Additionally, or alternatively, the invention concerns the use of at least one replication-competent and target cell lytic modified adenovirus according to the invention in the manufacture of a medicament to treat cancer.

Most preferably the cancer referred to herein includes any one or more of the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

It follows from the above that the invention concerns the use of a modified adenovirus—optimized for safety and survival—as an active adjuvant in a cancer treatment therapy that uses at least one and ideally two immunostimulatory agents i.e. OX40L & CD40L.

The modified adenovirus acts as an active adjuvant because it provides the danger signals required for an optimal immune response against a target peptide, but also retains its ability to oncolyse the cancer cells that it infects and replicates its genome in. The oncolytic cell killing is immunogenic by nature, which causes changes in the tumor microenvironment, that are likely to strengthen the immune response to the peptides/tumor.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

An embodiment of the present invention will now be described by way of example only with reference to the following wherein:

FIG. 1. shows an agarose electrophoresis analysis of the PCR amplified Gibson assembly reactions of the fragments GA-OX40L/F2A/CD40L and GA-OX40L/P2A/CD40L. In lane 1, a PCR amplification of the assembled fragments 1, 2 and 3 creating full length GA-OX40L/F2A/CD40L fragment the size of a 3974 bp. In lane 2, a PCR amplification of the assembled fragments 1, 2 and 3 creating full length GA-OX40L/P2A/CD40L fragment the size of a 3929 bp. In lane 3, a PCR amplification of the backbone virus plasmid pAd5/3D24 amplifying a fragment the size of a 3564 bp. Note that in both lanes 1 and 2 you can also see some amplification of the viral backbone.

FIGS. 2A-2B show the ability of the virus-produced OX40L protein to bind its receptor OX40 was confirmed by flow cytometry. An OX40 receptor antibody (rabbit) and a goat anti-rabbit antibody labeled with Alexa fluor 488 were used to bind the OX40L protein expressed from the viruses on the infected A549 cell surface. Unstained cells, uninfected stained cells and stained cells infected with virus without a transgene were used as negative controls. The data is presented as FIG. 2A) histogram or FIG. 2B) as mean of the absolute or proportional frequencies. The GM=Geometrical mean of cells positive for Alexa fluor 488 label, Freq parent=the proportion of cells positive for the Alexa fluor 488 label, Ctrl-virus=Ad5/3D24, a virus with an identical backbone and no transgene, OX40L-virus=The virus with OX40L only as a transgene, OX40L/CD40L.C1 and OX40L/CD40L.C3=viruses with OX40L and CD40L as transgenes.

FIG. 3. shows that OX40L able to bind receptor OX40 is expressed from Ad5/3-D24-OX40L-CD40.C1 (C1 in the figure) and Ad5/3-D24-OX40L-CD40.C3 (C3 in the figure) double transgene-viruses as well as from the virus expressing only OX40L-transgene (used as an expression control). Functional sandwich ELISA was used for the detection of native form of OX40L expressed from the viruses into the supernatant of infected cells. Supernatant from uninfected cells was used as a negative control. The dilutions are depicted for each sample in the figure.

FIG. 4. shows the functionality of the virus-expressed OX40L determined using OX40 receptor expressing HEK-293 cells with a reporter luciferase system. A virus without a transgene (Ctrl-virus), a virus with only OX40L as a transgene (OX40L-virus), viruses with OX40L and CD40L as transgenes (OX40L/CD40L.C1 and OX40L/CD40L.C3) were analyzed for their ability to bigger OX40L/OX40 interaction-dependent luciferase activity. A clear luciferase activity was detected with the OX40L-expressing viruses, indicating that the OX40L expressed from the virus genome is functional.

Figures 5A, 5B:
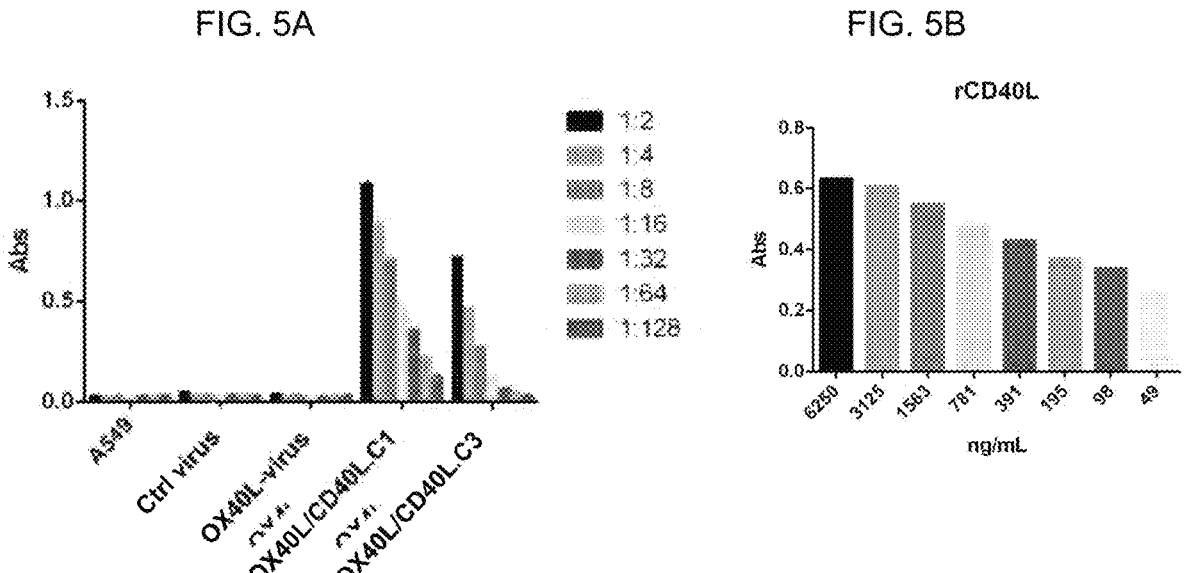

FIGS. 5A-5B show the absorbances measured using the Ramos Blue cell assay to determine functional CD40L expression levels. (FIG. 5A) The CD40L was expressed from the double transgene-viruses (OX40L/CD40L.Cland OX40L/CD40L.C3), and virus with no transgene (Ctrl virus) or OX40L as a single transgene (OX40L-virus), or non-infected cells (A549), were used as negative controls. (FIG. 5B) Absorbance measurements for the Ramos Blue cells treated with recombinant human CD40L.

Figures 6A, 6B, 6C:
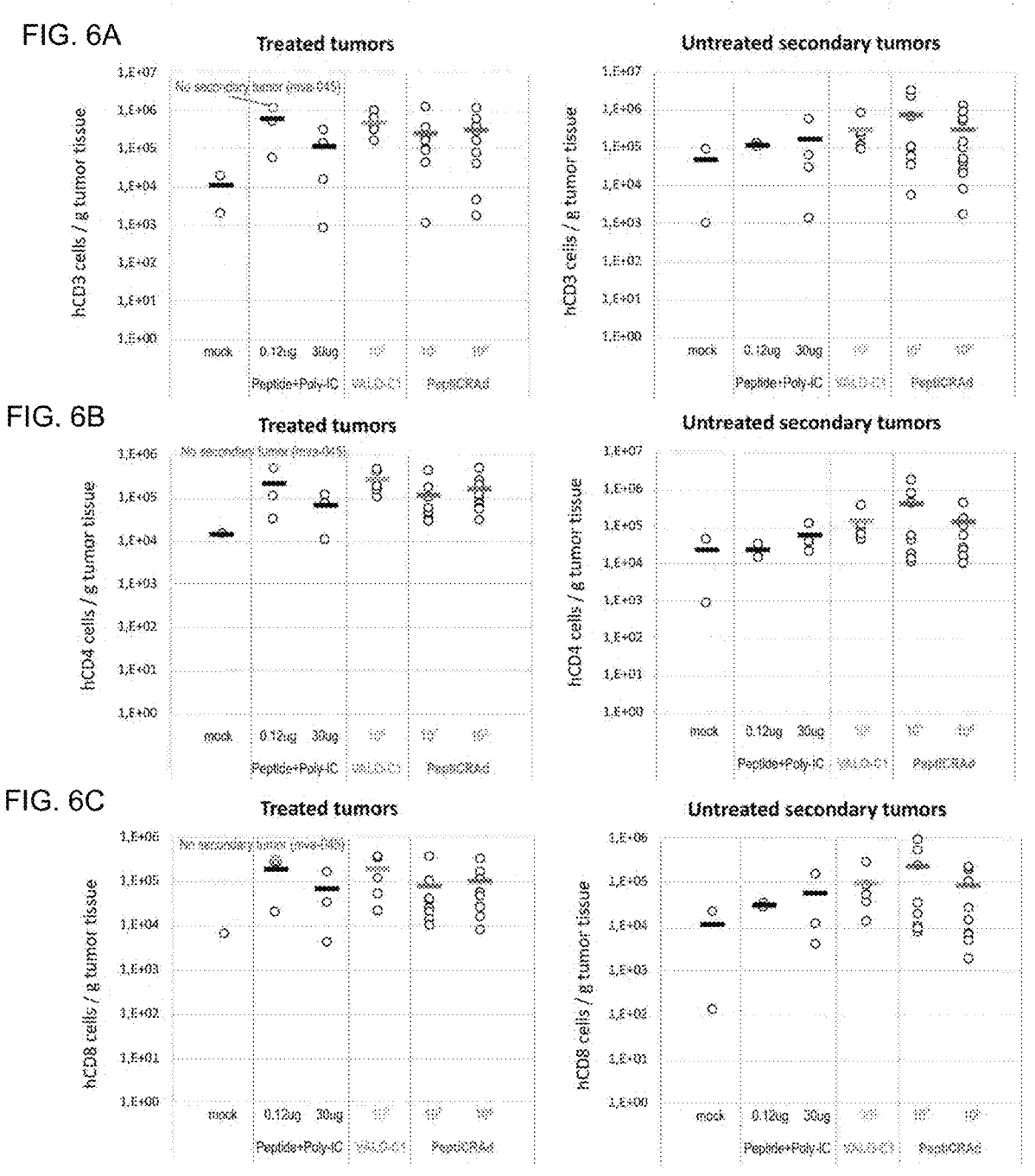

FIGS. 6A-6C show the frequency of T cells in treated and contralateral, untreated tumor when treated with oncolytic virus without peptide coating (VALO-C1), onclolytic virus with NYESO-1 or MAGE-A3-peptide antigen coating (Pep-tiCRAd) or peptide alone. The number of CD3+ T cells (FIG. 6A), CD4+ T cells (FIG. 6B) and CD8+ T cells (FIG. 6C) is depicted as cells per gram of tumor tissue in each treatment group. The treatments resulted in higher T cell frequencies in all groups compared to mock. The highest numbers were seen in tumors treated with VALO-C1 or PeptiCRAd.

FIGS. 74.78 show the frequency of all immune cells (CD45+ cells) in treated (Figure ZA) and contralateral, untreated (FIG. 7B) tumor when treated with oncolytic virus without peptide coating (VALO-C1), onclolytic virus with NYESO-1 or MAGE-A3 peptide antigen coating (Pepti-CRAd) or peptide alone. The frequencies were similar in all groups with a somewhat lower number in mock treated animals.

FIG. 8 shows the VALO-C1 and PeptiCRAd-treatments decrease the percentage of regulatory T-cells from all TILs in treated tumors.

FIG. 9 shows PeptiCRAd (containing OX40L- and CD40L-expressing virus coated with NY-ESO-1 and MAGE-A3 proteins) is able to stop tumor growth in human-ized mouse melanoma model even if the treatment is started for large, well established tumors. Experimental design: $2\times10^6$ SK-MEL-2 cells were implanted subcutaneously (one tumor per animal) into flank of NOD/Shi-scid/L-2Rγnull immunodeficient mice on day 1. On day 13, $5\times10^6$ PBMCs were injected intravenously. On day 16, $5\times10^4$ plasmacytoid and myeloid dendritic cells were injected intratumorally. Intratumoral PeptiCRAd treatments at a dose of $1\times10^9$ VP were given on days 16, 17, 18 (prime), and on day 25 (boost). First PeptiCRad dose was given immediately after DC injection. Tumor growth was followed. Animals were sacrificed on day 32. PeptiCRAd=Ad5/3-D24-OX40L-CD40L, an oncolytic adenovirus with 24 bp deletion in E1A, a 5/3 chimeric capsid and CD40L and OX40L transgenes expressed from the 14.7K locus, coated with NY-ESO-1 and MAGE-A3 peptides; OX40L PeptiCRAd=Ad5/3-D24-OX40L, an oncolytic adenovirus with 24 bp deletion in E1A, a 5/3 chimeric capsid and OX40L transgene expressed from the 14.7K locus, coated with NY-ESO-1 and MAGE-A3 peptides.

Figure 10:
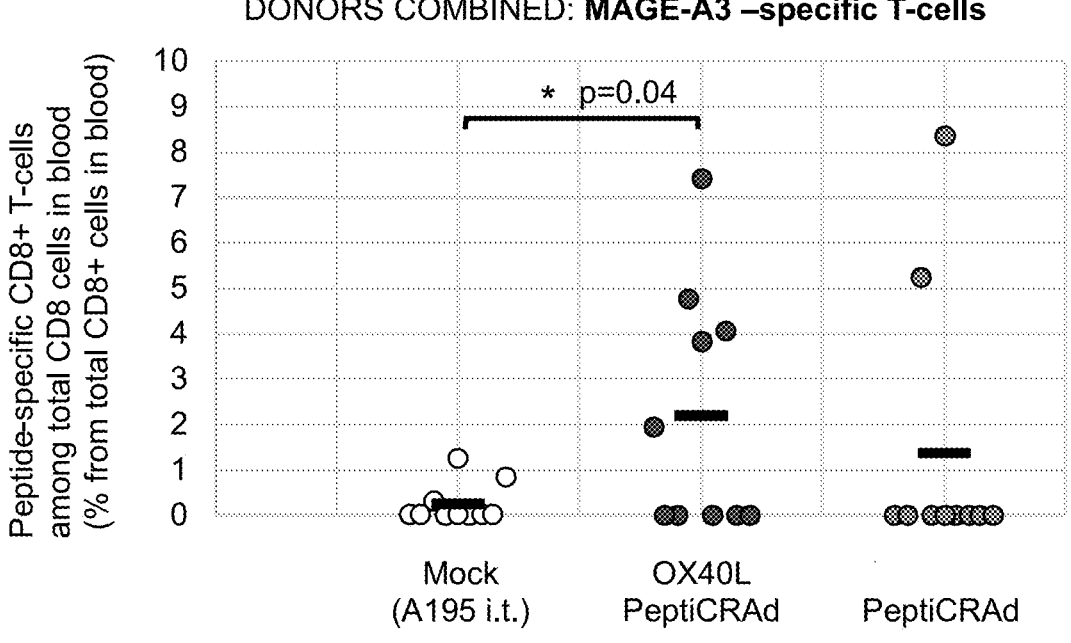

FIG. 10 shows OX40L(only)-PeptiCRAd increased the number of MAGE-A3-specific CD8+ T-cells in peripheral blood in comparison to mock treated animals. Two animals treated with PeptiCRAd also showed increased number of MAGE-A3 specific CD8+ T-cells in blood. Anti-MAGE-A3 T-cells were assessed by flow cytometry (pentamer analysis) at the end of the previously mentioned tumor growth study on day 32.

SPECIFIC DESCRIPTION

Materials and Methods:
Creation of an Oncolytic Adenovirus Having a E1A Gene Deletion of Nucleotides Encoding Amino Acids 923-946

The 24 base pair deletion was introduced into the Ad5 backbone sequence by using a shuttle plasmid targeting the E1A region, the cloning method described in Kanerva et al, the deletion first described in Fueyo et al.
Creation of an Oncolytic Adenovirus Having a 5/3 Chimeric Substitution of an Adenoviral Fiber Protein
The serotype 5 knob was replaced with the serotype 3 knob by using a shuttle plasmid with a modified fiber region to introduce the sequence via homologous recombination into the virus backbone. The specific cloning methods are described in Kanerva et al.

Creation of an oncolytic adenovirus having a 14.7k gene deletion of base pairs 30448-30834 with respect to the wild type adenovirus and wherein the sequence GGA GGA GAT GAC TGA (SEQ ID NO: 1) is substituted for GGA GGA GAC GAC TGA (SEQ ID NO: 2) and the creation of an oncolytic adenovirus having a gp19k gene deletion and a 7.1k gene deletion of base pairs 28541-29211 with respect to the wild type adenovirus.

The 14.7K deletion and the substitution of GGA GGA GAT GAC TGA (SEQ ID NO: 1) for GGA GGA GAC GAC TGA (SEQ ID NO: 2) (with the insertion of the transgene OX40L in the place of 14.7K) and the deletion of gp19k/7.1 k genes were introduced into a shuttle plasmid (pShuttle-OX40L) by chemical synthesis. Based on a virtual sequence designed in Vector NTI program, overlapping oligo nucleo-tides were designed at GeneArt (Thermo Fisher Scientific), that together comprised the whole sequence. Oligo synthesis was achieved by a solid phase synthesis applying controlled pore glass as the solid material. Oligos were then released to a liquid phase and assembled by using PCR on a fully automated assembly station. The synthetically cloned sequence was introduced into a pMX cloning vector, and verified by sequencing.
Cloning of OX40L and CD40L into pAD5/3-D24 for Obtaining pAd5/3-D24-OX40L/F2A/CD40L and pAd5/3-D24-OX40L/P2A/CD40L
To create viruses containing both OX40L and CD40L genes and either one of the foot-and-mouth disease virus 2A processing site (F2A) or Porcine teschovirus-1 2A process-ing site (P2A) inserted between the transgenes for co-translational processing, 3 fragments for each construct where amplified by PCR.

For F2A containing constructs, fragment 1 containing OX40L sequence and a part of the F2A processing site was amplified from pShuttle-OX40L using primers Gibson OX40L and F2A reverse OX40L (see list of all primers used in table 1), fragment 2 containing a part of the F2A pro-cessing site and the complete sequence of CD40L was amplified from pShuttle-CD40L using primers F2A forward CD40L and F2A reverse CD40L.

For P2A containing constructs, fragment 1 containing OX40L sequence and a part of the P2A processing site was amplified from pShuttle-OX40L using primers Gibson OX40L and P2A reverse OX40L (see list of all primers used in table 1), fragment 2 containing a part of the P2A pro-cessing site and the complete sequence of CD40L was amplified from pShuttle-CD40L using primers P2A forward CD40L and P2A reverse CD40L.

For both F2A and P2A constructs, fragment 3 containing adenovirus genomic sequence flanking the 3'end of CD40L was amplified from pShuttle-OX40L using primers F2A forward Adeno end w/o insertion and Gibson OX40L REV. All PCR reactions were performed with Phusion High-Fidelity DNA Polymerase (Thermo Fisher, F530) according to manufacturer's instructions followed by DpnI treatment (NEB, R0176). The reactions were purified with Nucleo- Spin® Gel and PCR Clean-up kit (MACHEREY-NAGEL, 740609.50). The purified fragments were then assembled together creating fragments GA-OX40L/F2A/CD40L and GA-OX40L/P2A/CD40L using Gibson assembly master mix (NEB, E2611) followed by PCR amplification of the assembled fragment using primers Gibson OX40L FW and Gibson OX40L REV (see FIG. 1 for agarose gel analysis of the final fragments).

To assemble GA-OX40L/F2A/CD40L or GA-OX40L/P2A/CD40L into the viral backbone, pAd5/3-D24 was digested with SrfI (NEB, R0629L) and BarI (SibEnzyme®, E548) followed by ethanol precipitation. The digested viral backbone pAd5/3-D24 was assembled with GA-OX40L/F2A/CD40L or GA-OX40L/P2A/CD40L fragments using Gibson assembly master mix (NEB, E2611) according to the manufacturer's instructions to generate pAd5/3-D24-OX40L/F2A/CD40L and pAd5/3-D24-OX40L/P2A/CD40L. The Gibson assembly reactions were transformed into NEB® 5-alpha Competent E. coli (NEB, C2987H) according to manufacturer's instructions. Positive colonies were screened by PCR and the correct recombination events were further confirmed by sequencing the constructs.

Cloning of CD40L and OX40L into pAD53-D24 for Obtaining pAd5/3-D24-CD40L-OX40L

To create a fragment including CD40L (CD40L-GA) to be cloned into the viral backbone pAd5/3-D24 by specific homologous recombination reaction (brand name Gibson Assembly, New England Biolabs), three PCR products were first assembled together with Gibson assembly recombination reaction. The fragments fused together contained the following sequences: Fragment A corresponds to nucleotides 21376 to 22114 of pAd5/3-D24 plasmid. Fragment B corresponds to nucleotides 999 to 2623 of pShuttle-CD40L plasmid. Fragment C corresponds to nucleotides 22820-27107 of pAd5/3-D24 plasmid (see table 1b-3b for list of primers and primer sequences used). PCR reactions were performed with Phusion High-Fidelity DNA Polymerase (Thermo Fisher, F530) according to manufacturer's instructions and the reactions were purified with NucleoSpin® Gel and PCR Clean-up kit (MACHEREY-NAGEL, 740609.50). Next, to create CD40L-GA, the purified PCR fragments were assembled together by the Gibson Assembly recombination reaction according to manufacturer's instructions (Gibson assembly master mix, NEB E2611). After the homologous recombination, the newly created CD40L-GA fragment was further amplified by PCR using the primers AA and DD (for the primer sequences, please see tables 1b and 3b) using Phusion High-Fidelity DNA Polymerase according to manufacturer's instructions. The PCR amplified CD40L-GA was gel purified using NucleoSpin® Gel and PCR Clean-up kit. To clone CD40L-GA into the viral backbone, pAd5/3-D24 was digested with SpeI (NEB, R0133S) and AsiSI (NEB,R0630S) followed by ethanol precipitation. The digested viral backbone pAd5/3-D24 was assembled with CD40L-GA fragment using Gibson assembly master mix (NEB, E2611) according to the manufacturer's instructions to generate pAd5/3-D24-CD40L. The Gibson assembly reaction was transformed into NEB® 5-alpha Competent E. coli (NEB, C2987H) according to manufacturer's instructions. Positive colonies were screened by PCR and the correct recombination was further confirmed by sequencing the constructs. In order to create the final construct, i.e. virus containing both CD40L and OX40L genes, a fragment including OX40L (OX40L-GA) was amplified using the following primers: Gibson OX40L FW and Gibson OX40L REV (amplifying the region in pShuttle-OX40L corresponding to nucleotides 11 to 3287), please see table 4b for primer sequences. PCR reaction was performed with Phusion High-Fidelity DNA Polymerase (Thermo Fisher, F530) according to manufacturer's instructions and the reactions was purified with NucleoSpin® Gel and PCR Clean-up kit (MACHEREY-NAGEL, 740609.50). To clone OX40L-GA into the viral backbone, pAd5/3-D24-CD40L was digested with SrfI (NEB, R0629L) and BarI (SibEnzyme®, E548) followed by ethanol precipitation. The digested viral backbone pAd5/3-D24-CD40L was assembled with OX40L-GA fragment using Gibson assembly master mix (NEB, E2611) according to the manufacturer's instructions to generate pAd5/3-D24-CD40L-OX40L. The Gibson assembly reaction was transformed into NEB® 5-alpha Competent E. coli (NEB, C2987H) according to manufacturer's instructions. Positive colonies were screened by PCR and the correct recombination was further confirmed by sequencing the constructs.

Figure 2:
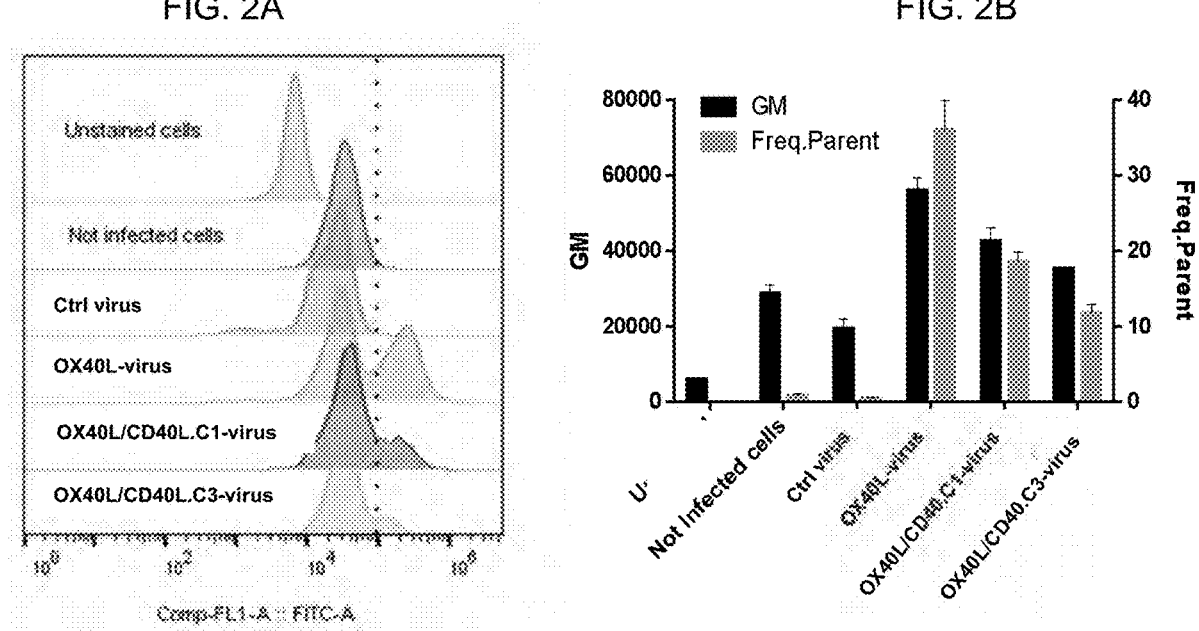

Methods for the In Vitro Testing of the Modified Adenovirus with One Transgene or Two Transgenes Flow Cytometric Analysis to Determine OX40L/OX40 Interaction A flow cytometric analysis was performed to verify that the OX40L expressed from the viruses is able to bind its native receptor OX40 (FIG. 2). Human A549 cells were plated on a 6-well-plate and infected with the double transgene viruses (Ad5/3-D24-OX40L-CD40L.C1 and Ad5/3-D24-OX40L-CD40L.C3, termed as OX40L/CD40L.C1 and OX40L/CD40L.C3), the virus with OX40L only (Ad5/3-D24-OX40L, termed as OX40L-virus in the figures) or a virus with no transgenes (Ad5/3-D24, termed as ctrl-virus) with a multiplicity of infection of 10 (i.e. 10 viruses per cell).

72 hours after the infection, the cells were collected and counted, and $3 \times 10^5$ cells were plated per well on a 96-well-plate in duplicates. The plate was centrifuged at 400 g for 5 minutes and re-suspended in PBS. This step was repeated twice, and the cells were then suspended into a mixture of OX40 receptor antibody and goat anti-rabbit Alexa fluor 488 antibody, incubated for 30 minutes, washed 3 times and then ran in BD Accuri flow cytometer to detect the geometric mean of the OX40L/OX40 complex cells. The data was analyzed with the FlowJo software.

Sandwich ELISA to Verify the OX40L/OX40 Interaction

To further verify that the OX40L expressed from the viruses is able to bind its native receptor, OX40, a functional sandwich ELISA was performed (FIG. 3). A 96-well-plate was coated with 2 ug/ml OX40 receptor in its native form overnight and subsequently washed 3 times with a 0.05% Tween20 v/v in PBS. Supernatant from virus-infected A549 cells was added to the wells and the plate was incubated in 37° C. for 1 hour, and subsequently washed again 3 times.

The wells were incubated for 1 hour with a mouse anti-human OX40L antibody (1:1000 dilution in PBS), washed 3 times, and incubated with an anti-mouse-HRP conjugate (1:1000 dilution in PBS) for 1 hour. After washing the plates 3 times, 90 μl of TMB substrate was added and the plate was incubated in the dark at room temperature for 10 minutes. The HRP conjugated to the anti-mouse antibody reacts with the substrate TMB calorimetrically, and the intensity of the color was measured at 450 nm spectrophotometrically.

Functionality Assay with OX40/NF-kB—HEK293 Recombinant Cell Line

To verify that the OX40L produced by the viruses (either the single transgene viruses or the double transgene viruses) is functional and able to activate the downstream signals when binding its receptor, OX40, a functionality assay using human embryonic kidney cell line 293 (HEK-293) constitutively expressing OX40 was performed (FIG. 4).

OX40L product is produced in the culture medium of an A549 cell culture infected with a virus expressing OX40L gene. The medium is collected and added to a culture of OX40/NF-κB Reporter—HEK293 cells constitutively expressing the OX40 receptor. The binding of OX40L to OX40 receptor triggers an intracellular signaling pathway that, via NF-κB activation, leads to the expression of firefly Luciferase reporter gene. The luciferase activity is measured using the ONE-step luciferase assay system and a luminometer to determine the relative bioluminescence of a known concentration of OX40L standard. The OX40L concentration of the virus sample can then be analyzed based on the luminescence readings and the standard curve. Before the OX40L concentration can be determined, a standard curve for OX40L has to be defined using known concentrations of recombinant human OX40L.

Briefly, $1.5 \times 10^4$ A549 cells were plated on a 96-well-plate in 10% DMEM. On the following day A549 cells were infected with a multiplicity of infection of 10 i.e. 10 viruses per cell, with either the single transgene virus (Ad5/3-D24-OX40L, termed as OX40L-virus in the figures), the double transgene viruses (Ad5/3-D24-OX40L-CD40L.C1 and Ad5/3-D24-OX40L-CD40L.C3, termed as OX40L/CD40L.C1 and OX40L/CD40L.C3) or a virus without a transgene (Ad5/3-D24, termed as ctrl-virus) in 2% DMEM.

Some wells were left uninfected to be used as a negative control. 72 hours after the infection, the cells were centrifuged at 500 g for 5 minutes, the media was disposed and $2 \times 10^5$ OX40/NF-kB-HEK293 cells in 100 ul of 10% MEM was added on top of the A549 cells. After centrifuging with 400 g for 1 minute the cells were incubated at 37° C. for 6 hours before lysing with a lysis buffer and adding 20 ul of each lysate on a transparent 96-well-plate wells. After adding 100 ul of the luciferase reagent as a substrate, the luminescence was immediately read on a luminometer.

Functionality Assay for the CD40L Transgene Product

To verify that the CD40L protein expressed from the double-transgene viruses is able to bind its native receptor CD40 and activate downstream signals on the CD40 expressing cells, a Ramos Blue cell-based functionality assay was performed (FIG. 5).

Ramos Blue is a B lymphocyte cell line that stably expresses an NF-κB-inducible SEAP (secreted embryonic alkaline phosphatase) reporter gene. The CD40L product is produced in the culture medium of a cell culture infected with a PeptiCRAd virus expressing CD40L gene. The medium is collected and added to a culture of Ramos Blue cells constitutively expressing the CD40 receptor. The binding of CD40L to CD40 triggers an intracellular signaling pathway that leads to the secretion of SEAP which turns a substrate blue, and that can be measured spectrophotometrically at 620-655 nm. The relative concentration of the functional CD40L is determined by using a standard curve for recombinant human CD40L.

Briefly, human A549 cells were plated on a 6-well-plate and infected with the double transgene viruses (OX40L/CD40L.C1 or OX40L/CD40L.C3), the virus with only OX40L (OX40L-virus) as a transgene or a virus with no transgenes (Ctrl-virus) with a multiplicity of infection of 10. Supernatant was collected 72 hours later and any cells and cell debris was removed by centrifugation at 500 g for 5 minutes. A 2-fold dilution series were prepared from the supernatants and of the recombinant CD40L protein with a starting concentration of 100 ug/ml. A 100 μl of each supernatant was added to $4 \times 10^5$ Ramos Blue cells in 96 well plate (plated in 100 μl) and the plate was incubated at 37° C. for 18 hours. After incubation, the cells were pelleted by centrifuging at 400 g for 5 minutes, and 40 μl of the supernatant was added to a new 96-well plate. 160 μl of the QUANTI-Blue substrate was added, the plate was incubated for 1 hour and the SEAP level was determined spectrophotometrically.

Methods for the In Vivo Testing of the Modified Adenovirus with and without Peptide Antigen Coating NOD/Shi-scid/IL-2Rγnull immunodeficient mice were humanized using hematopoietic stem cells (CD34+, HLA-B35+) isolated from human cord blood. A375 human melanoma tumors were implanted subcutaneously ($2 \times 10^6$ cells per 100 ul) and the animals were randomized into groups based on the humanization rate and the tumor size. The animals were treated oncolytic virus without peptide coating (VALO-C1) or nclolytic virus with peptide antigen coating (PeptiCRAd) (virus dose $1 \times 10^8$ for both groups; a suboptimal dose of $1 \times 10^7$ was also tested for PeptiCRAd). Peptide vaccines (0.12 or 30 ug) were given intradermally with Poly-IC as an adjuvant.

The treatments started 25 days after randomization (D0) by a bolus dose of cyclophosphamide (1 mg/mouse i.v.). Treatments were given intratumorally (mock, virus and PeptiCRAd) or intradermally (peptide control) on days 1, 2, 3 and 12. Secondary tumors were implanted into the contralateral flank two days after the third treatment (day 5). No treatments for secondary tumors were given.

Peripheral blood mononuclear cells (PBMCs) and tumor infiltrating CD8+ lymphocytes (TILs) were analyzed for peptide antigen NY-ESO-1 and MAGE-specific CD8+ T-cells by flow cytometry with dextramer analysis. Different immune cell subsets among PBMCs and TILs were assessed. The flow cytometric analysis were performed on Attune NxT Flow Cytometer (Life Technologies).

PBMC Mouse Model Immunization 35 eight-week old NOD-Prkdcem26Cd52/IL-2Rγ em26Cd22/NjuCrl immunodeficient mice (NCG) were engrafted with $2 \cdot 10^6$ SKMEL-2 tumor cells (HLA-B35+) on the right flank (Day 0). On day 13, $5 \times 10^6$ HLA-B35+ human peripheral blood mononuclear cells (PBMC) from two different donors were injected intravenously. Intratumoral treatments with NYESO-1 and MAGE-A3-complexed 5/3 capsid and containing OX40L-expressing virus ("OX40L PeptiCRAd") or a NYESO-1 and MAGE-A3-complexed 5/3 capsid containing OX40L- and CD40L-expressing virus ("PeptiCRAd")—were initiated on Day 16 with a virus dose of $1 \times 10^9$ VP complexed with each peptide. Concomitantly with the first PeptiCRAd treatment, 50'000 autologous plasmacytoid and myeloid dendritic cells were injected intratumorally. On days 17, 18 (prime with the first treatment) and 25 (boost), the tumors were treated with intratumoral PeptiCRAd injections without addition of dendritic cells. The treatment schema is presented in FIG. 10. Tumor growth was followed. Animals were sacrificed on day 32. OX40L-PeptiCRAd and PeptiCRad contains a 24 bp deletion in E1A, a deleted gp19k/7.1K region, a human OX40L transgene expressed from the 14.7K locus and a 5/3 chimeric fiber.

Results

Functionality of the OX40L Expressed from the Viruses

The flow cytometric analysis as well as the sandwich ELISA indicate that the OX40L transgene product expressed from the viruses onto the cell surface of the infected cell, as well as shed to some extent from the cell surface, is able to bind its receptor OX40 (FIGS. 2 and 3, respectively). Most importantly, when analyzing the functionality of the OX40L expressed from the viruses, a clear downstream gene activation was seen when utilizing HEK-293 cells stably expressing OX40 receptor (FIG. 4). The binding of OX40L to OX40 triggers an intracellular signaling pathway in these cells, which via NF-κB activation leads to the expression of firefly Luciferase reporter gene. The levels of bioluminescence obtained with using the A549 cells infected with OX40L-expressing viruses clearly indicate that the OX40L protein is functional and activates the downstream signaling when binding to OX40, when compared to the bioluminescence levels obtained using a virus without a transgene or negative cell controls.

Functionality of the CD40L Expressed from the OX40L/CD40L-Expressing Viruses

A clear downstream gene activation was seen when analyzing the CD40L functionality utilizing Ramos Blue cells stably expressing CD40 receptor (FIG. 5). The binding of CD40L to CD40 triggers an intracellular signaling pathway in these cells, which via NF-κB activation leads to the expression of SEAP gene. The absorbance levels obtained when using the A549 cells infected with CD40L-expressing viruses clearly indicate that the CD40L protein is functional and activates the downstream signaling when binding to CD40, when compared to the absorbance levels obtained using viruses without CD40L as a transgene or negative cell controls.

Modified Oncolytic Virus with and without Peptide Surface Antigen Elicits Peptide Specific Immune Response in a Humanized Mouse Model All active treatments (peptide alone, virus without peptide [VALO-C1], and virus with peptide [PeptiCRAd]) increased the number of immune cells in primary tumors in comparison to mock treated animals. Both VALO-C1 and Pepti-CRAd-1 treated animals showed more T-cells (CD3, CD4, CD8) in primary tumors in comparison to peptide vaccine or mock treated animals post treatment, while the number of overall infiltrating immune cells (CD45) was similar in all groups (FIGS. 6 and 7, respectively).

Furthermore, the number of T regulatory cells (CD3+/CD4+/FoxP3+) was smaller in VALO-C1 and PeptiCRAd-1 treated primary tumors in comparison to primary tumors from peptide vaccine or mock treated animals (FIG. 8). This suggests that intratumorally administered immunogenic adenovirus (either naked virus VALO-C1 or PeptiCRAd-1) modulates the tumor microenvironment by reducing local immune-suppression.

Oncolytic adenovirus with (PeptiCRAd) or without peptide antigen (VALO-C1) is superior to standard peptide vaccination in triggering systemic tumor-targeted CD8+ T-cell responses and infiltration of CD8+ TILs into untreated distant tumors. The data suggest that PeptiCRAd improves the tumor targeting specificity of a standard oncolytic virus.

PeptiCRAd Elicits Peptide-Specific Immune Response in a PBMC Mouse Model

Treatments with NY-ESO-1- and MAGE-A3-complexed PeptiCRAd resulted in tumor growth arrest in humanized mouse melanoma model even when the treatment was started for large, well established tumors (FIG. 9). The mice treated with OX40L-PeptiCRAd showed significantly more MAGE-A3-specific CD8+ T cells among all CD8+ T cells of the PBMCs than mock treated mice, indicating that the PeptiCRAd-treatment was able to elicit peptide-specific response in humanized mice (FIG. 10).

REFERENCES

Kanerva et al 2003 Mol Ther 12:449-458.
Fueyo et al 2000. Oncogene 19:2-12.

TABLE 1

Primers used for the
cloning of pAd5/3-D24-CD40L-OX40L.

| Primer name | Primer sequence |
|---|---|
| P2A rev OX40L | 5'CGCCGGCCTGCTTCAGCAGGCTGAAGTTGGT GGCGCCGCTGCCGCTCCTCCTCTTCCTAAGGAC ACAGAATTCACCAGG3' (SEQ ID NO: 4) |
| P2A fwd CD40L | 5'AGCGGCGCCACCAACTTCAGCCTGCTGAAGC AGGCCGGCGACGTGGAGGAGAACCCCGGCATGA TCGAAACATACAACCAAAC3' (SEQ ID NO: 5) |

TABLE 1-continued

Primers used for the
cloning of pAd5/3-D24-CD40L-OX40L.

| Primer name | Primer sequence |
|---|---|
| F2A fwd Adeno end without insertion | 5'ACTCAAACTCTGATAAAAAAAAATAATAAAG CATCACTTACTTAAAATCAGTTAGCAAATTTCT GTCC3' (SEQ ID NO: 6) |
| F2A rev OX40L | 5'TCGAAGTTCAGGGTCTGCTTCACGGGGGCCA CGATCTTCTGCTTGTGCCTGGCCTCGCCGCTGC CGCTCCTCCTCTTCCTAAGGACACAGAATTCAC CAGG3' (SEQ ID NO: 7) |
| F2A fwd CD40L | 5'AGAAGATCGTGGCCCCCGTGAAGCAGACCCT GAACTTCGACCTGCTGAAGCTGGCCGGCGACGT GGAGAGCAACCCCGGCCCCATGATCGAAACATA CAACCAAAC3' (SEQ ID NO: 8) |
| F2A rev CD40L | 5'-TAAGTGATGCTTTATTATTTTTTTTTATCA GAGTTTGAGTAAGCCAAAGGACGTGAAGCCAG3' (SEQ ID NO: 9) |
| Gibson OX40L FW | 5'GCCGAAGTTCAGATGACTAACTCAG3' (SEQ ID NO: 10) |
| Gibson OX40L REV | 5'ATAGTGGGTGCGGATGGACAG3' (SEQ ID NO: 11) |

TABLE 1b

Primers to PCR fragment
A with pAd5/3D24 as template.

| Name | Sense sequence | Primer 5'-3' | Tm | Position at pAd5/3D24 |
|---|---|---|---|---|
| Primer AA | ACCGCAGTTGA CAGCATTACC (SEQ ID NO: 12) | ACCGCAGTT GACAGCATT ACC (SEQ ID NO: 13) | 57.9 | 21376-21396 |
| Primer BB | TCCACGCCTT TGCCAACTGG (SEQ ID NO: 14) | CAGTTGGCA AAGGCGTGG (SEQ ID NO: 15) | 57.5 | 22097-22114 |

TABLE 2b

Primers to PCR fragment
B with pShuttle-CD40L as template.

| Name | Sense sequence | Primer 5'-3' | Tm | Position at pShuttle-CD40L |
|---|---|---|---|---|
| Primer CC | GCCTGTGGACT ATTCTGCTGC (SEQ ID NO: 16) | GCCTGTGGA CTATTCTGC TGC (SEQ ID NO: 17) | 58.3 | 999-1019 |
| Primer B | GTCTGGGCGTT AGGATACAGC (SEQ ID NO: 18) | GCTGTATCC TAACGCCCA GAC (SEQ ID NO: 19) | 57.5 | 2603-2623 |

TABLE 3b

| | | | | Position at |
|---|---|---|---|---|
| Name | Sense sequence | Primer 5'-3' | Tm | pAd5/3D24 |
| Primer C | GCACCGTAGTG GCATCAAAAGG (SEQ ID NO: 20) | GCACCGTAG TGGCATCAA AAGG (SEQ ID NO: 21) | 58.3 | 22820- 22841 |
| Primer DD | CTACGTCATCT CCAGCGGC (SEQ ID NO: 22) | GCCGCTGGA GATGACGTA G (SEQ ID NO: 23) | 57.9 | 27089- 27107 |

Primers to PCR fragment C with pAd5/3-D24 as template.

TABLE 4b

| | | | | Position at |
|---|---|---|---|---|
| Name | Sense sequence | Primer sequence (5'→3') | Tm (° C.) | OX40L Block |
| Gibson OX40L FW | GCCGAAGTTCA GATGACTAACT CAG (SEQ ID NO: 24) | GCCGAAGTT CAGATGACT AACTCAG (SEQ ID NO: 25) | 62 | 11-37 |
| Gibson OX40L REV | CTGTCCATCCG CACCCACTAT (SEQ ID NO: 26) | ATAGTGGGT GCGGATGGA CAG (SEQ ID NO: 27) | 62 | 3167- 3187 |

Primers to PCR OX40L insert with pShuttle-CX40L as template.

The invention claimed is:

1. A modified replicating adenovirus (Ad) of serotype 5 (Ad5) having lytic activity in target cancer cells comprising:
   a) a E1A gene deletion wherein the deletion is of nucleotides encoding amino acids 923-946 with respect to the wild-type Ad5 sequence;
   b) a 5/3 chimeric substitution of a knob of an adenoviral fiber protein wherein the knob of Ad5 is replaced by the knob of a serotype 3 Ad (Ad3);
   c) a 14.7k gene deletion wherein the deletion is of base pairs 30448-30834 with respect to the wild type Ad5 sequence and wherein the sequence GGA GGA GAT GAC TGA (SEQ ID NO: 1) is substituted for GGA GGA GAC GAC TGA (SEQ ID NO: 2);
   d) a gp19k gene deletion and a 7.1k gene deletion wherein the deletions are of base pairs 28541-29211 with respect to the wild type Ad5 sequence; and
   e) an insertion of a molecule encoding OX40L and a molecule encoding CD40L in the E3B region, replacing the 14.7K gene deletion, wherein the molecule encoding CD40L is inserted immediately downstream from the molecule encoding OX40L using a 2A processing site, and the 2A processing site is preceded by a cleavage site and a SGSG-linker (SEQ ID NO: 28) to ensure effective cleavage of OX40L and CD40L.

2. The modified adenovirus according to claim 1 wherein said OX40L is human OX40L.

3. The modified adenovirus according to claim 1 wherein said CD40L is human CD40L.

4. The modified adenovirus according to claim 1 wherein said 2A processing site is a foot-and-mouth disease virus 2A processing site (F2A) or a porcine teschovirus-1 2A processing site.

5. The modified adenovirus according to claim 1 wherein a molecule encoding the whole cDNA of each of OX40L and CD40L is inserted into said adenovirus.

6. A pharmaceutical composition comprising at least one modified replication-competent and target cell lytic adenovirus according to claim 1 and a suitable carrier.

7. The pharmaceutical composition according to claim 6 wherein said composition is formulated for intratumoral, intramuscular, intra-arterial, intravenous, intrapleural, intravesicular, intradermal, intracavitary or peritoneal injection, or an oral administration.

8. A method of treating cancer in a patient comprising administering to a patient an effective amount of a composition comprising at least one modified replication-competent and target cell lytic adenovirus according to claim 1.

9. The method of treating cancer according to claim 8 wherein the at least one modified replication-competent and target cell lytic adenovirus is administered with a cell checkpoint modulator.

10. The method of treating cancer according to claim 9 wherein the checkpoint modulator is an anti-PD1 molecule, an anti-PD-L1 molecule or an anti-CTLA-4 molecule.

11. The method according to claim 8 wherein said cancer is selected form the list comprising or consisting of: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

* * * * *

SEQUENCE LISTING

<160> NUMBER OF SEQ ID NOS: 29

<210> SEQ ID NO 1
<211> LENGTH: 15
<212> TYPE: DNA
<213> ORGANISM: Homo sapiens

<400> SEQUENCE: 1
ggaggagatg actga                                                      15

<210> SEQ ID NO 2
<211> LENGTH: 15
<212> TYPE: DNA
<213> ORGANISM: Homo sapiens

<400> SEQUENCE: 2
ggaggagacg actga                                                      15

<210> SEQ ID NO 3
<211> LENGTH: 22
<212> TYPE: DNA
<213> ORGANISM: Homo sapiens

<400> SEQUENCE: 3
ggaggagatg actgattagg ta                                              22

<210> SEQ ID NO 4
<211> LENGTH: 79
<212> TYPE: DNA
<213> ORGANISM: Homo sapiens

<400> SEQUENCE: 4
cgccggcctg cttcagcagg ctgaagttgg tggcgccgct gccgctcctc ctcttcctaa    60
ggacacagaa ttcaccagg                                                  79

<210> SEQ ID NO 5
<211> LENGTH: 83
<212> TYPE: DNA
<213> ORGANISM: Homo sapiens

<400> SEQUENCE: 5
agcggcgcca ccaacttcag cctgctgaag caggccggcg acgtggagga gaaccccggc    60
atgatcgaaa catacaacca aac                                             83

-continued

```
<210> SEQ ID NO 6
<211> LENGTH: 68
<212> TYPE: DNA
<213> ORGANISM: Homo sapiens

<400> SEQUENCE: 6
actcaaactc tgataaaaaa aaataataaa gcatcactta cttaaaatca gttagcaaat      60
ttctgtcc                                                              68

<210> SEQ ID NO 7
<211> LENGTH: 101
<212> TYPE: DNA
<213> ORGANISM: Homo sapiens

<400> SEQUENCE: 7
tcgaagttca gggtctgctt cacgggggcc acgatcttct gcttgtgcct ggcctcgccg      60
ctgccgctcc tcctcttcct aaggacacag aattcaccag g                         101

<210> SEQ ID NO 8
<211> LENGTH: 106
<212> TYPE: DNA
<213> ORGANISM: Homo sapiens

<400> SEQUENCE: 8
agaagatcgt ggcccccgtg aagcagaccc tgaacttcga cctgctgaag ctggccggcg      60
acgtggagag caaccccggc cccatgatcg aaacatacaa ccaaac                    106

<210> SEQ ID NO 9
<211> LENGTH: 62
<212> TYPE: DNA
<213> ORGANISM: Homo sapiens

<400> SEQUENCE: 9
taagtgatgc tttattattt tttttttatca gagtttgagt aagccaaagg acgtgaagcc     60
ag                                                                    62

<210> SEQ ID NO 10
<211> LENGTH: 25
<212> TYPE: DNA
<213> ORGANISM: Homo sapiens

<400> SEQUENCE: 10
gccgaagttc agatgactaa ctcag                                           25

<210> SEQ ID NO 11
<211> LENGTH: 21
<212> TYPE: DNA
<213> ORGANISM: Homo sapiens

<400> SEQUENCE: 11
atagtgggtg cggatggaca g                                              21

<210> SEQ ID NO 12
<211> LENGTH: 21
<212> TYPE: DNA
<213> ORGANISM: Homo sapiens

<400> SEQUENCE: 12
accgcagttg acagcattac c                                              21
```

-continued

```
<210> SEQ ID NO 13
<211> LENGTH: 21
<212> TYPE: DNA
<213> ORGANISM: Homo sapiens

<400> SEQUENCE: 13
accgcagttg acagcattac c                                        21

<210> SEQ ID NO 14
<211> LENGTH: 20
<212> TYPE: DNA
<213> ORGANISM: Homo sapiens

<400> SEQUENCE: 14
tccacgcctt tgccaactgg                                          20

<210> SEQ ID NO 15
<211> LENGTH: 18
<212> TYPE: DNA
<213> ORGANISM: Homo sapiens

<400> SEQUENCE: 15
cagttggcaa aggcgtgg                                            18

<210> SEQ ID NO 16
<211> LENGTH: 21
<212> TYPE: DNA
<213> ORGANISM: Homo sapiens

<400> SEQUENCE: 16
gcctgtggac tattctgctg c                                        21

<210> SEQ ID NO 17
<211> LENGTH: 21
<212> TYPE: DNA
<213> ORGANISM: Homo sapiens

<400> SEQUENCE: 17
gcctgtggac tattctgctg c                                        21

<210> SEQ ID NO 18
<211> LENGTH: 21
<212> TYPE: DNA
<213> ORGANISM: Homo sapiens

<400> SEQUENCE: 18
gtctgggcgt taggatacag c                                        21

<210> SEQ ID NO 19
<211> LENGTH: 21
<212> TYPE: DNA
<213> ORGANISM: Homo sapiens

<400> SEQUENCE: 19
gctgtatcct aacgcccaga c                                        21

<210> SEQ ID NO 20
<211> LENGTH: 22
<212> TYPE: DNA
<213> ORGANISM: Homo sapiens

<400> SEQUENCE: 20
gcaccgtagt ggcatcaaaa gg                                       22
```

-continued

<210> SEQ ID NO 21
<211> LENGTH: 22
<212> TYPE: DNA
<213> ORGANISM: Homo sapiens

<400> SEQUENCE: 21
gcaccgtagt ggcatcaaaa gg                                                    22

<210> SEQ ID NO 22
<211> LENGTH: 19
<212> TYPE: DNA
<213> ORGANISM: Homo sapiens

<400> SEQUENCE: 22
ctacgtcatc tccagcggc                                                        19

<210> SEQ ID NO 23
<211> LENGTH: 19
<212> TYPE: DNA
<213> ORGANISM: Homo sapiens

<400> SEQUENCE: 23
gccgctggag atgacgtag                                                        19

<210> SEQ ID NO 24
<211> LENGTH: 25
<212> TYPE: DNA
<213> ORGANISM: Homo sapiens

<400> SEQUENCE: 24
gccgaagttc agatgactaa ctcag                                                 25

<210> SEQ ID NO 25
<211> LENGTH: 25
<212> TYPE: DNA
<213> ORGANISM: Homo sapiens

<400> SEQUENCE: 25
gccgaagttc agatgactaa ctcag                                                 25

<210> SEQ ID NO 26
<211> LENGTH: 21
<212> TYPE: DNA
<213> ORGANISM: Homo sapiens

<400> SEQUENCE: 26
ctgtccatcc gcacccacta t                                                     21

<210> SEQ ID NO 27
<211> LENGTH: 21
<212> TYPE: DNA
<213> ORGANISM: Homo sapiens

<400> SEQUENCE: 27
atagtgggtg cggatggaca g                                                     21

<210> SEQ ID NO 28
<211> LENGTH: 4
<212> TYPE: PRT
<213> ORGANISM: Artificial Sequence
<220> FEATURE:
<223> OTHER INFORMATION: linker -continued

```
<400> SEQUENCE: 28

Ser Gly Ser Gly
1

<210> SEQ ID NO 29
<211> LENGTH: 4
<212> TYPE: PRT
<213> ORGANISM: Artificial Sequence
<220> FEATURE:
<223> OTHER INFORMATION: furin cleavage site

<400> SEQUENCE: 29

Arg Lys Arg Arg
1
```